US008703051B2

(12) United States Patent
Trabalka et al.

(10) Patent No.: US 8,703,051 B2
(45) Date of Patent: Apr. 22, 2014

(54) SANITIZING HEADSETS DURING A PERIOD OF NON-USE

(71) Applicants: Stephen Trabalka, Cedar Grove, NJ (US); Martin Siegel, Englewood Cliffs, NJ (US); David Kyhl, Leonia, NJ (US)

(72) Inventors: Stephen Trabalka, Cedar Grove, NJ (US); Martin Siegel, Englewood Cliffs, NJ (US); David Kyhl, Leonia, NJ (US)

(73) Assignee: Vcom International Multimedia Corporation, Fairfield, NJ (US)

( * ) Notice: Subject to any disclaimer, the term of this patent is extended or adjusted under 35 U.S.C. 154(b) by 0 days.

(21) Appl. No.: 14/072,337

(22) Filed: Nov. 5, 2013

(65) Prior Publication Data

US 2014/0056758 A1    Feb. 27, 2014

Related U.S. Application Data

(62) Division of application No. 13/533,065, filed on Jun. 26, 2012, now Pat. No. 8,597,588.

(51) Int. Cl.
*A61L 2/00* (2006.01)
*H01J 37/00* (2006.01)

(52) U.S. Cl.
USPC .......... 422/24; 422/300; 250/455.11

(58) Field of Classification Search
USPC ............... 422/24, 300; 250/455.11
See application file for complete search history.

(56) References Cited

U.S. PATENT DOCUMENTS

| 2,225,817 | A | 12/1940 | Arnold |
| 2,235,296 | A | 3/1941 | Muncheryan |
| 2,822,476 | A | 2/1958 | Osgood |
| 3,776,694 | A | 12/1973 | Leittl |
| 3,885,987 | A | 5/1975 | Keister et al. |
| 3,955,922 | A | 5/1976 | Moulthrop |
| 4,465,907 | A | 8/1984 | Minear et al. |
| 4,906,851 | A | 3/1990 | Beasley et al. |
| 5,160,699 | A | 11/1992 | Siegal |
| 5,225,172 | A | 7/1993 | Meyler et al. |
| 6,096,264 | A | 8/2000 | Peifer |
| 2012/0275967 | A1 | 11/2012 | Yokoi et al. |

FOREIGN PATENT DOCUMENTS

CN            201674643 U1    12/2010

*Primary Examiner* — Kevin Joyner
(74) *Attorney, Agent, or Firm* — Arthur Jacob

(57) ABSTRACT

A method for sanitizing headsets during a period of non-use by placing the headsets on a support construct in the form of a rack within which there is a source of ultraviolet radiation. The headsets are mounted straddling the rack, gripping the rack to be secured in place with a resilient biasing force. Then, the rack, with mounted headsets, is enclosed within a case, suitable for storage or transport. The source is activated to pass ultraviolet radiation through the rack to impinge upon the headsets, during a timed duration of operation, with the case automatically locked closed for that duration, thereby sanitizing the headsets. Reflective surfaces within the case serve effectively to immerse the headsets within ultraviolet radiation for the duration of operation, and air is circulated within the case, passing through the rack, during the sanitizing operation to assure complete sanitizing of the headsets.

16 Claims, 5 Drawing Sheets

US 8,703,051 B2

SANITIZING HEADSETS DURING A PERIOD OF NON-USE

This is a division of application Ser. No. 13/533,065, filed Jun. 26, 2012, now U.S. Pat. No. 8,597,588, the entire disclosures of which are incorporated herein by reference thereto.

The present invention relates generally to the sanitizing of headsets during a period of non-use and pertains, more specifically, to apparatus and method providing convenient sanitizing of headsets, such as those ordinarily used in connection with various listening stations, during a period when the headsets are not in use.

Listening stations are quite common and are found in a variety of settings such as, for example, schools and other educational facilities, business conferences, trade shows and various expositions where multiple headsets are distributed among students, business executives and attendees at a wide variety of shows and expositions where information is distributed through individual headsets to be worn by a multitude of users. A problem faced by such uses of headsets is the prevention of transmitting harmful micro-organisms through the passing of headsets from user to user. For example, educators have long been concerned that students utilizing listening centers might transmit harmful micro-organisms from student to student through the interchange of headsets associated with such listening centers.

The present invention provides a convenient, effective and dependable solution to the problem of dealing with the potential transmission of harmful micro-organisms through the use of headsets by multiple users. To that end, the present invention provides apparatus and method that take advantage of the well-established ability of ultraviolet radiation to serve as an effective agent in destroying harmful micro-organisms. Short-wavelength ultraviolet radiation (UVC) long has been identified as a "germicidal UV" and it is this ultraviolet germicidal radiation that is employed by the present invention to solve the problem outlined above. As such, the present invention attains several objects and advantages, some of which are summarized as follows: Provides a relatively simple and highly practical apparatus and method for eliminating the transfer of harmful micro-organisms otherwise occasioned by the communal use of headsets among multiple users; conveniently and quickly sanitizes multiple headsets used in connection with listening stations, during periods of non-use of the headsets; enables the convenient handling of headsets, as well as other components of a listening center, while effectively sanitizing the headsets during periods of non-use; conducts the sanitizing of headsets between uses at a listening station with a high degree of safety; enables a simplified procedure for accomplishing the sanitization of multiple headsets with increased ease and efficiency; provides for the convenient storage and transport of a plurality of headsets, as well as additional components of a listening center, while accomplishing effective sanitizing of the headsets; promotes the health and well-being of users of a listening center, and especially children in educational settings, with minimal effort and maximum effectiveness; enables ease of use and ready maintenance for long-term, effective operation; provides an apparatus of rugged, yet relatively simple and economical construction capable of exemplary performance over an extended service life.

The above objects and advantages, as well as further objects and advantages, are attained by the present invention, which may be described briefly as a method for sanitizing headsets during a period of non-use, each headset including at least one headphone and a headband, the method comprising: mounting the headsets on a support construct, in captured engagement with the support construct, the support construct extending in a longitudinal direction along a prescribed length and having a lateral width and an altitudinal height providing an exterior contour configuration, an interior, and a lateral cross-sectional configuration for the reception of a plurality of headsets mounted and secured in the captured engagement in a row longitudinally along the exterior of the support construct, with each headset straddling the support construct laterally to engage and place the support construct beneath each headset, with each headphone and headband in juxtaposition with the interior of the support construct; activating a source of ultraviolet radiation located within the interior of the support construct; passing ultraviolet radiation from the interior through the support construct to the headsets mounted upon the support construct; and selectively enclosing the support construct and the headsets within an enclosure subsequent to mounting the headsets along the support construct, and prior to activating the source of ultraviolet radiation, such that upon enclosing the headsets mounted upon the support construct within the enclosure and activating the source of ultraviolet radiation, ultraviolet radiation is directed to the headsets for sanitizing the headsets within the enclosure.

The invention will be understood more fully, while still further objects and advantages will become apparent, in the following detailed description of preferred embodiments of the invention illustrated in the accompanying drawing, in which.

Figure 1:
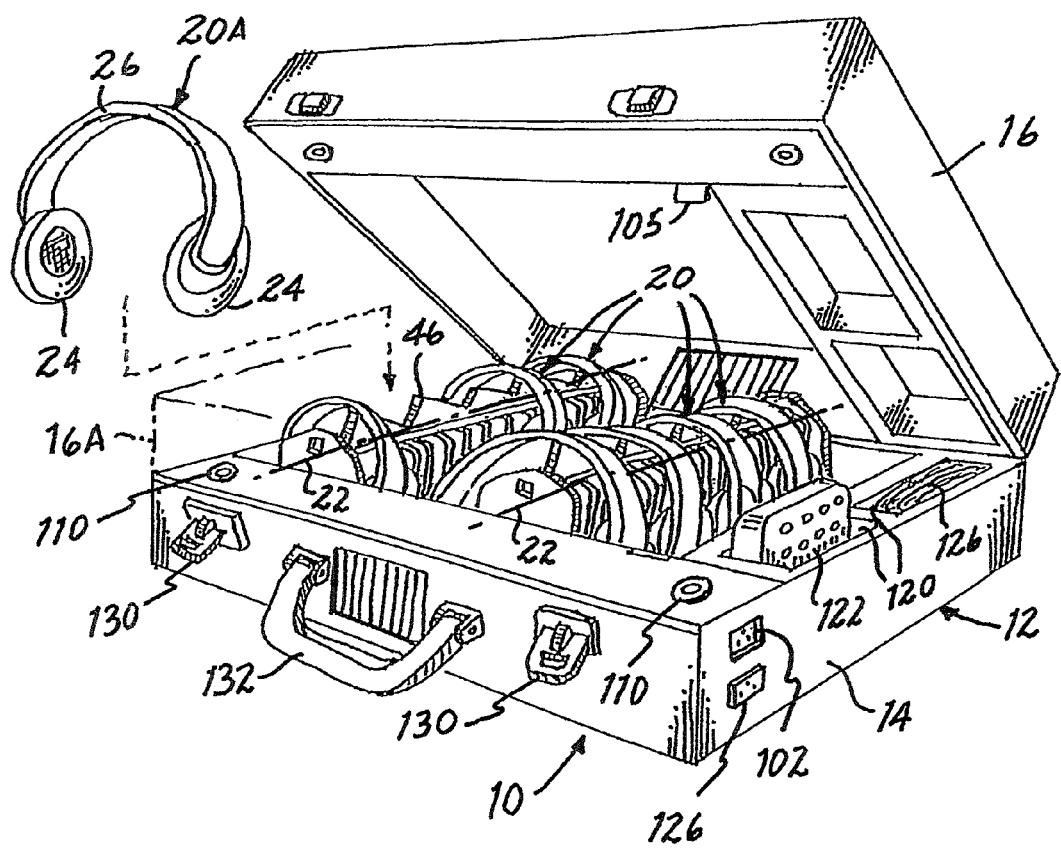
FIG. 1 is a partially diagrammatic, pictorial view of an apparatus constructed for use in accordance with the present invention, shown partially open to reveal inner details.
Figure 2:
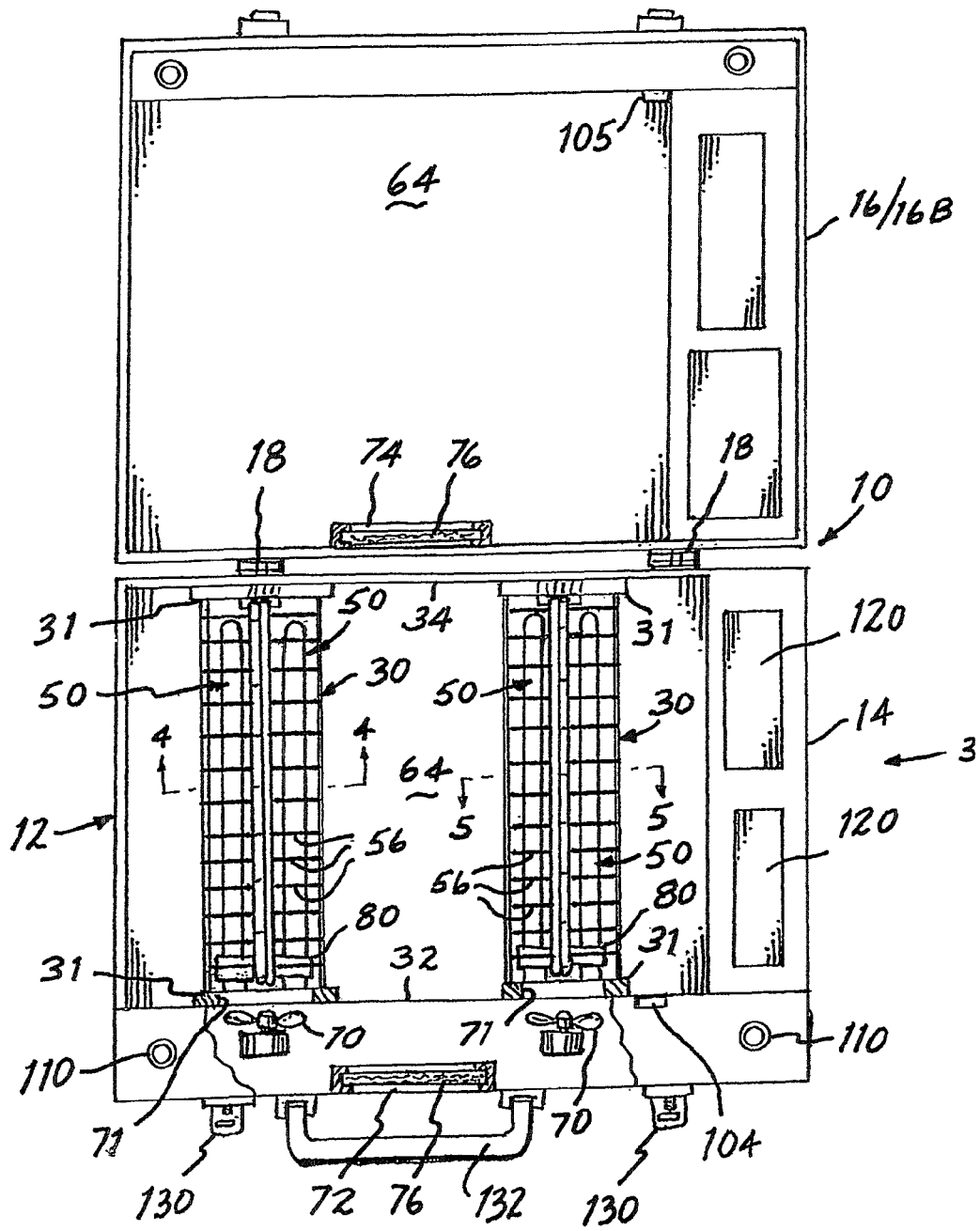
FIG. 2 is a partially diagrammatic, plan view of the apparatus shown fully open.
Figure 3:
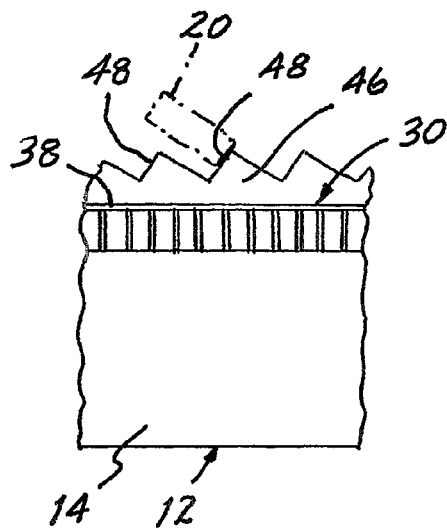
FIG. 3 is a an enlarged, fragmentary side elevational view of a portion of the apparatus, taken in the direction of the arrow 3 in FIG. 2.

Referring now to the drawing, and especially to FIGS. 1 through 3 thereof, an apparatus constructed for use in accordance with the present invention is shown at 10 and is seen to include an enclosure, shown in the form of a case 12 having a receptacle 14 and a cover 16 hinged to the receptacle 14 by hinges 18 that enable the cover 16 to be moved selectively between a closed position, as illustrated in phantom at 16A in FIG. 1, and a fully open position, as shown at 16B in FIG. 2. A plurality of headsets 20, when not in use, are to be enclosed within the interior of case 12, some of which headsets 20 being shown already placed within receptacle 14, in rows 22, while one headset 20A is shown outside case 12, about to be placed within the case 12. Headsets 20 are of conventional construction, each headset 20 including a pair of headphones 24 mounted upon a headband 26. Headband 26 has a resiliently flexible construction and is arranged to resiliently bias the headphones 24 toward one another, in a now conventional manner While some headsets can include an attached microphone, headsets 20 are of the type that do not include a microphone. Apparatus 10 will accommodate headsets with or without an attached microphone. Likewise, both wireless and wired headsets readily are accommodated.

Figure 4:
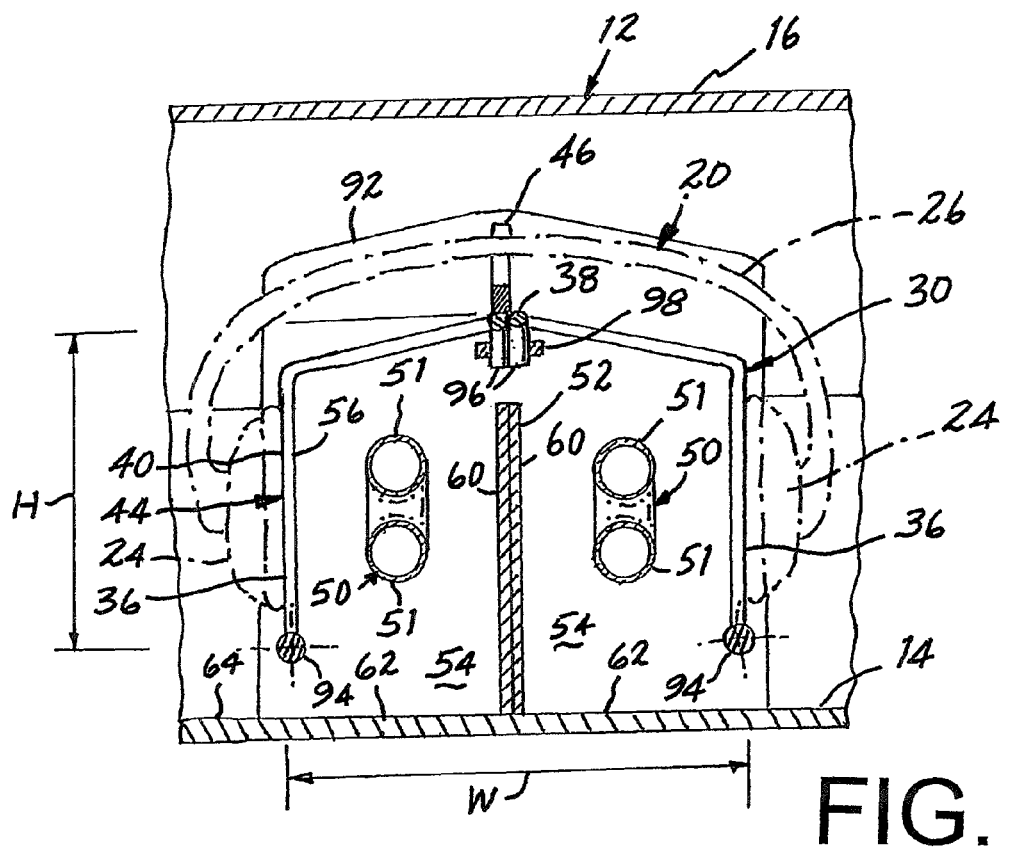
FIG. 4 is a further enlarged cross-sectional view taken along line 4-4 of FIG. 2, showing the apparatus closed and component parts in a first position.

Each row 22 of headsets 20 is supported within receptacle 14 by a support construct shown in the form of a rack 30 which extends in a longitudinal direction along a prescribed length between opposite ends 31 placed respectively adjacent a front 32 and a rear 34 of the receptacle 14. As best seen in FIG. 4, each rack 30 has a lateral width W between laterally opposite sides 36, and an altitudinal height H extending to a top 38, providing an exterior 40 and an interior 42, the exterior 40 following an exterior contour configuration establishing a lateral cross-sectional configuration 44 dimensioned and configured for the reception of a plurality of headsets 20 mounted in corresponding row 22. A notched rail 46 extends longitudinally along the top 38 of each rack 30 and includes longitudinally spaced-apart shoulders 48 for engaging the headsets 20 of a row 22 to maintain the headsets 20 spaced from one another along the corresponding row 22. At the same time, width W and height H are such that each headset 20 is retained in place, draped over a rack 30, straddling the rack 30, with the corresponding headphones 24 spaced apart and biased by the resilient nature of the intervening headband 26 essentially to clamp and thereby hold the headset 20 in place, secured in captured engagement with the rack 30, with the headband 26 engaged with a corresponding shoulder 48. In this manner, headsets 20 are retained securely in place, spaced apart longitudinally along each row 22, in captured engagement with rack 30, with the headphones 24 confronting the interior 42 of a corresponding rack 30.

A source of ultraviolet radiation is located within the interior 42 of each rack 30 and is shown in the form of lamps 50, each having tubular legs 51 extending longitudinally along each rack 30 in juxtaposition with each side 36 of the rack 30. In the preferred arrangement, a central partition 52 divides each interior 42 into laterally adjacent compartments 54, and the legs 51 of each lamp 50 are located within a compartment 54, legs 51 extending parallel to one-another, with each lamp 50 juxtaposed with a corresponding side 36. Lamps 50, when activated, provide short-range, short-wavelength ultraviolet radiation (UVC) known to be effective against harmful micro-organisms, and considered "germicidal UV".

Each rack 30 is structured for passing UVC radiation from the interior 42 to the headsets 20 mounted upon the exterior 40 of the rack 30. In the illustrated preferred construction, each rack 30 includes a cage-like construction in which generally arch-shaped bars 56 lie in planes transverse to the longitudinal direction of a rack 30 to establish the lateral cross-sectional configuration 44 of each rack 30. Bars 56 are spaced apart longitudinally so that radiation from lamps 50 then can pass between the longitudinally spaced-apart bars 56, from the interior 42 of each rack 30 to the exterior 40, and thus impinge upon the headband 26 and headphones 24 of each headset 20, thereby effecting sanitization of the headsets 20. The cage-like construction of each rack 30 provides racks 30 with sufficient strength to support the plurality of headsets 20 maintained in alignment along rows 22, in clamped engagement with each rack 30, while enabling the effective transmission of UVC radiation from lamps 50 to headsets 20. At the same time, headsets 20 remain secured in place on each rack 30 during handling and transport of apparatus 10.

When it is desired to sanitize a plurality of headsets 20, during a period of non-use of such headsets 20, the headsets 20 are placed within receptacle 14 as described above, and case 12 is closed. Lamps 50 then are activated and UVC radiation is directed toward the headsets 20. In the illustrated preferred construction, reflective surfaces 60 and 62, capable of reflecting UVC radiation, are provided along each central partition 52 and beneath each leg 51 of each lamp 50, respectively, to maximize the transmission of UVC radiation from each lamp 50, through each corresponding rack 30, to the headsets 20 mounted upon the rack 30. In order further to enhance exposure of each headset 20 to the UVC radiation, interior surfaces 64 of the case 12 are provided with reflective characteristics capable of reflecting UVC radiation impinging upon these surfaces. Thus, each headset 20 essentially is fully exposed to UVC radiation from multiple directions and thereby immersed in UVC radiation distributed essentially evenly among the plural headsets 20 for effective sanitization of every headset 20.

In the preferred arrangement, the sanitizing of headsets 20 is enhanced still further by circulating air through the interior of case 12 and about the headsets 20 within the interior of case 12 during the sanitizing process. Circulation of air within the case 12 assures that even the most resistant micro-organisms will be exposed to radiation sufficient to break down these micro-organisms quickly and effectively. To that end, an air mover, shown in the form of a blower fan 70, is placed in juxtaposition with an end 31 of each rack 30 and is aligned with an aperture 71 communicating with the corresponding interior 42 of each rack 30 such that upon actuation, each blower fan 70 will draw ambient air through an adjacent intake opening 72 and will direct intake air through a corresponding aperture 71 and into a respective bank of headsets 20 mounted along a row 22. The air then will pass between the spaced-apart bars 56 to be circulated about each headset 20 for increased effectiveness of the sanitization process. Air drawn into case 12 is exhausted through an exhaust opening 74. An air filter 76, such as an HEPA filter, is juxtaposed with each of the intake opening 72 and the exhaust opening 74 to assure that no micro-organisms will escape from the interior of case 12 to the ambient atmosphere. In addition, air filter 76 at intake opening 72 assures that contaminants are precluded from entering case 12 during the sanitizing process.

Figure 5:
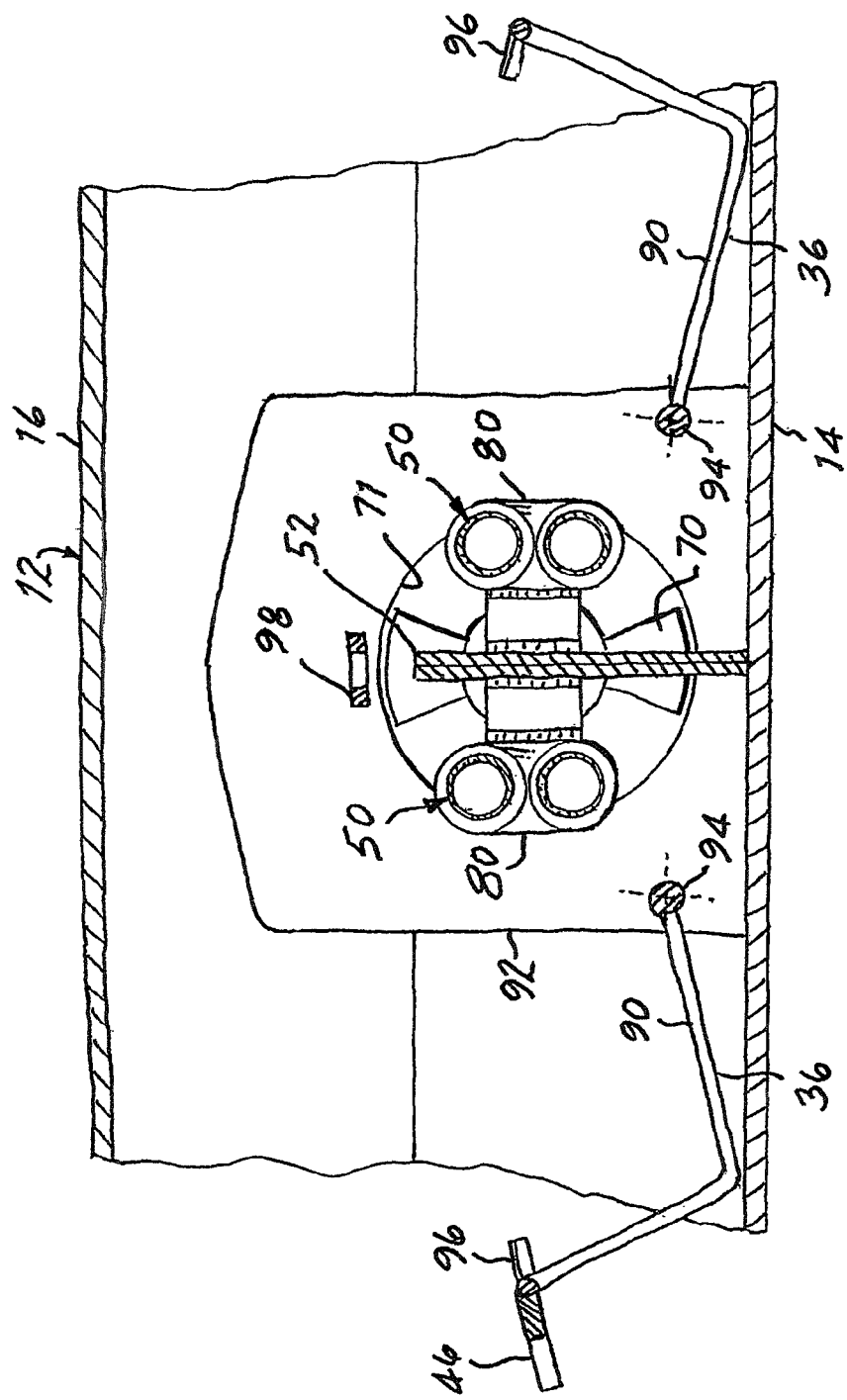
FIG. 5 is a similarly enlarged cross-sectional view taken along line 5-5 of FIG. 2, showing the apparatus closed and the component parts in a second position.

Turning now to FIG. 5, as well as to FIGS. 2 and 4, each lamp 50 is held within a corresponding compartment 54 by fixtures 80, in a conventional manner, fixtures 80 being mounted upon central partition 52. Should it become necessary to replace or otherwise perform maintenance on a lamp 50, each rack 30 is constructed for facilitating selective access to corresponding lamps 50. To that end, the cage-like construction of each rack 30 includes a "clamshell-like" arrangement in which bars 56 are divided into side members 90 along each side 36, and each side member 90 is mounted between end plates 92 by means of pins 94 integral with the side members 90 and journaled within end plates 92, for pivotal movement of side members 90 between a closed position, as shown in FIG. 4, and an open position, as illustrated in FIG. 5. With the side members 90 in the open position, lamps 50 are exposed for ready maintenance or removal and replacement. With the side members 90 in the closed position, selectively releasable catch members 96 are engaged with a catch 98 carried by a corresponding end plate 92 to retain the side members 90 in place for receiving headsets 20, as described above.

Figure 6:
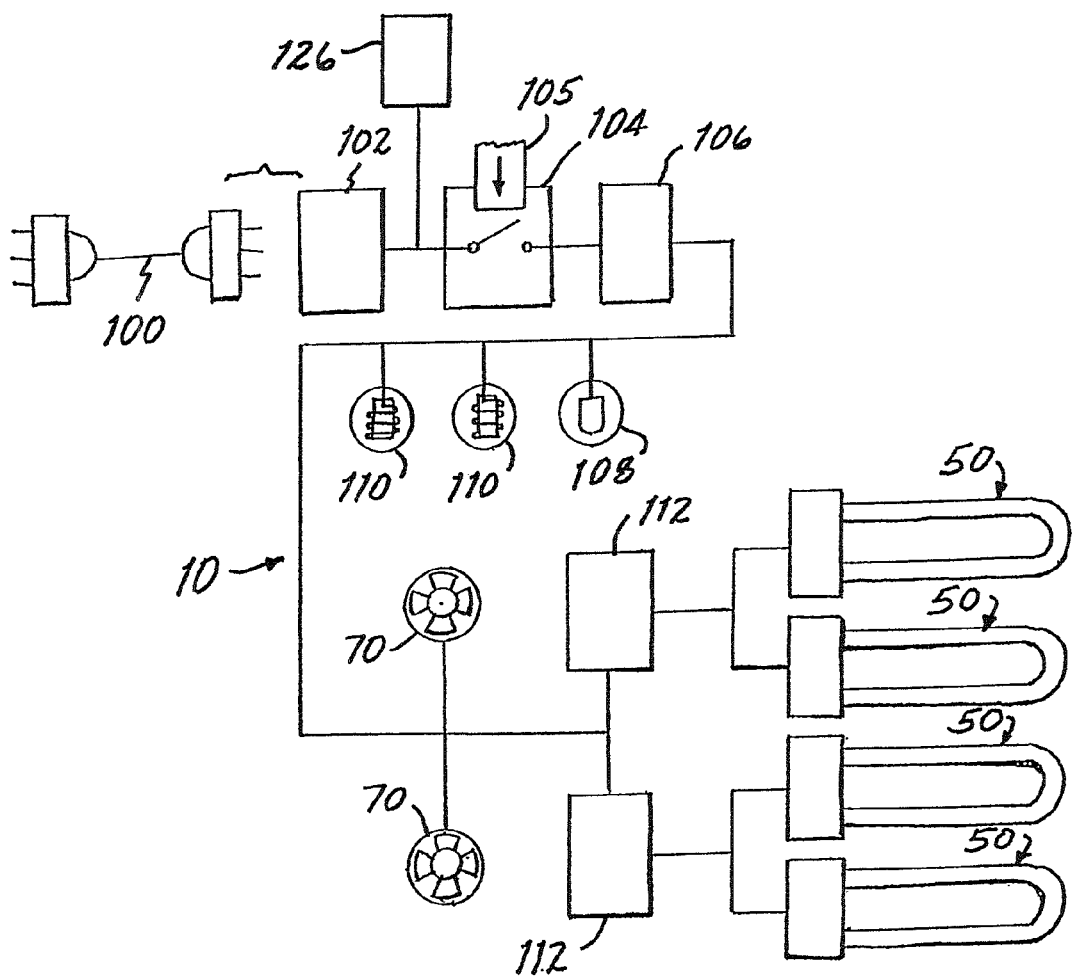
FIG. 6 is a somewhat schematic diagram illustrating the arrangement of components of the apparatus.

Referring now to FIG. 6, as well as to FIGS. 1 and 2, apparatus 10 is powered through a separable line cord 100 provided for connection to a power entry receptacle 102 which, in turn, is connected, through an interlock switch 104, to a timing device 106. In response to closing the case 12, interlock switch 104 is closed by an actuator 105 carried by cover 16 (also see FIGS. 1 and 2) and power is supplied through interlock switch 104 to timing device 106 which is activated to begin a timed cycle of operation. An indicator lamp 108 confirms that the operating cycle has begun, and a pair of magnetic locking mechanisms 110 are activated to lock the case 12 closed and maintain the case 12 closed throughout the duration of the timed cycle of operation. At the same time, power is supplied to a pair of ballasts 112 which activate lamps 50, and blower fans 70 are actuated to circulate ambient air through the interior of the case 12. During the timed cycle of operation, the case 12 remains locked against opening, by virtue of the activation of the magnetic locking mechanisms 110, thus preventing inadvertent opening of the case 12 and any concomitant deleterious consequences that might result from the escape of ultraviolet radiation, such as the exposure of persons in the vicinity to ultraviolet radiation. Upon completion of the timed cycle of operation, the indicator lamp 108 will confirm completion of the operation and the magnetic locking mechanisms will be de-activated, enabling the case 12 to be opened for access to the now-sanitized headsets 20. Inadvertent operation of lamps 50 while case 12 is open is precluded by the interlock switch 104, so that activation of lamps 50 is limited to the condition where case 12 is fully closed and ready for a sanitization operation.

Returning now to FIGS. 1 and 2, case 12 includes auxiliary compartments 120 for receiving ancillary components of a listening station, such as a jackbox and connector cables, shown at 122 and 124, respectively, as well as the line cord 100 when not in use. In addition, an auxiliary outlet 126 is included for convenience. Latches 130 are provided for maintaining case 12 closed when apparatus 10 is not in use, and a carrying handle 132 facilitates transport of the latched-closed apparatus 10, along with headsets 20 and ancillary components utilized at a listening station. In this connection, it is noted that the cage-like construction of racks 30 combines strength with light-weight, contributing to the portability of apparatus 10. However, it will be apparent that apparatus 10 may be constructed in a form that provides the same sanitization process in a fixed installation.

It will be seen that the present invention attains all of the objects and advantages summarized above, namely: Provides a relatively simple and highly practical apparatus and method for eliminating the transfer of harmful micro-organisms otherwise occasioned by the communal use of headsets among multiple users; conveniently and quickly sanitizes multiple headsets used in connection with listening stations, during periods of non-use of the headsets; enables the convenient handling of headsets, as well as other components of a listening center, while effectively sanitizing the headsets during periods of non-use; conducts the sanitizing of headsets between uses at a listening station with a high degree of safety; enables a simplified procedure for accomplishing the sanitization of multiple headsets with increased ease and efficiency; provides for the convenient storage and transport of a plurality of headsets, as well as additional components of a listening center, while accomplishing effective sanitizing of the headsets; promotes the health and well-being of users of a listening center, and especially children in educational settings, with minimal effort and maximum effectiveness; enables ease of use and ready maintenance for long-term, effective operation; provides an apparatus of rugged, yet relatively simple and economical construction capable of exemplary performance over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which and exclusive property or privilege is claimed are defined as follows:

1. A method for sanitizing headsets during a period of non-use, each headset including at least one headphone and a headband, the method comprising:
   mounting the headsets on a support construct, in captured engagement with the support construct, the support construct extending in a longitudinal direction along a prescribed length and having a lateral width and an altitudinal height providing an exterior contour configuration, an interior, and a lateral cross-sectional configuration for the reception of a plurality of headsets mounted and secured in the captured engagement in a row longitudinally along the exterior of the support construct, with each headset straddling the support construct laterally to engage and place the support construct beneath each headset, with each headphone and headband in juxtaposition with the interior of the support construct;
   activating a source of ultraviolet radiation located within the interior of the support construct;
   passing ultraviolet radiation from the interior through the support construct to the headsets mounted upon the support construct; and
   selectively enclosing the support construct and the headsets within an enclosure subsequent to mounting the headsets along the support construct, and prior to activating the source of ultraviolet radiation, such that upon enclosing the headsets mounted upon the support construct within the enclosure and activating the source of ultraviolet radiation, ultraviolet radiation is directed to the headsets for sanitizing the headsets within the enclosure.

2. The method of claim 1 including locking the enclosure during activation of the source of ultraviolet radiation.

3. The method of claim 1 wherein activation of the source of ultraviolet radiation is for a timed duration.

4. The method of claim 1 wherein activation of the source of ultraviolet radiation is for a timed duration, and the method includes locking the enclosure throughout the timed duration.

5. The method of claim 1 including circulating air through the interior of the support construct while the source of ultraviolet radiation is active.

6. The method of claim 1 including drawing air into the enclosure, circulating air so drawn, through the interior of the support structure while the source of ultraviolet radiation is active, exhausting air so circulated, from the enclosure while the source of ultraviolet radiation is active, and filtering air so exhausted, as the air is exhausted.

7. The method of claim 1 including reflecting ultraviolet radiation from at least one reflector placed within the support construct, from the interior of the support construct toward the headsets mounted upon the support construct, when the source of ultraviolet radiation is active.

8. The method of claim 1 including reflecting ultraviolet radiation from interior surfaces of the enclosure toward the headsets mounted upon the support construct, when the enclosure encloses the support construct and the source of ultraviolet radiation is active.

9. The method of claim 1 including providing the support construct with a cage-like structure including a plurality of spaced-apart bars following the exterior contour configuration of the support construct to enclose the source of ultraviolet radiation within the interior of the support construct while enabling the passage of ultraviolet radiation from the interior, through the cage-like structure, to the headsets mounted on the cage-like structure, and circulating air through the interior of the support construct while the source of ultraviolet radiation is active.

10. A method for sanitizing headsets during a period of non-use, wherein each headset includes at least one headphone carried by a resiliently flexible headband having a given configuration, the method comprising:

mounting the headsets on a support construct extending in a longitudinal direction between opposite ends, along a prescribed length and having a lateral width and an altitudinal height providing an exterior with an exterior contour configuration, an interior, and a lateral cross-sectional configuration for the reception of a plurality of headsets mounted and secured in captured engagement in a row extending longitudinally along the exterior of the support construct, with the headband of each headset flexed resiliently out of the given configuration by the lateral width and altitudinal height of the support construct to establish a resilient biasing force biasing each mounted headset into the captured engagement with the support construct to maintain each mounted headset secured in place, straddled laterally over the exterior contour configuration of the support construct with the support construct beneath each headset and each headphone and headband in captured juxtaposition with the interior of the support construct;

activating a source of ultraviolet radiation located within the interior of the support construct;

passing ultraviolet radiation from the interior of the support construct through the support construct to headsets mounted upon the support construct; and selectively enclosing the support construct and the headsets within an enclosure subsequent to mounting the headsets along the support construct, such that upon enclosing the headsets mounted upon the support construct within the enclosure and activation of the source of ultraviolet radiation, ultraviolet radiation is directed to the headsets for sanitizing the headsets within the enclosure.

11. The method of claim 10 including providing the support construct with a cage-like structure including a plurality of spaced-apart bars following the exterior contour configuration of the support construct to enclose the source of ultraviolet radiation within the interior of the support construct while enabling the passage of ultraviolet radiation from the interior, through the cage-like structure, to the headsets mounted upon the cage-like structure.

12. The method of claim 11 including circulating air into the interior of the support construct at one end of the opposite ends and out of the interior between the spaced-apart bars of the cage-like structure while the source of ultraviolet radiation is active.

13. The method of claim 12 including drawing air into the enclosure through an intake, exhausting air from the enclosure through an exhaust, and filtering at least a corresponding one of air drawn into the enclosure and air exhausted from the enclosure.

14. The method of claim 13 including filtering air drawn into the enclosure, and filtering air exhausted from the enclosure.

15. The method of claim 10 including reflecting ultraviolet radiation from at least one reflector placed within the support construct, from the interior of the support construct toward the headsets mounted upon the support construct, when the source of ultraviolet radiation is active.

16. The method of claim 10 including reflecting ultraviolet radiation from interior surfaces of the enclosure toward the headsets mounted upon the support construct, when the enclosure encloses the support construct and the source of ultraviolet radiation is active.

* * * * *